(12) United States Patent
Hauck et al.

(10) Patent No.: US 9,592,132 B2
(45) Date of Patent: Mar. 14, 2017

(54) SHAPE-MEMORY SPINAL FUSION SYSTEM

(71) Applicant: Shape Memory Orthopedics, Windsor, CA (US)

(72) Inventors: Brian Albert Hauck, Windsor, CA (US); Robert Trigg McClellan, Los Gatos, CA (US)

(73) Assignee: Shape Memory Orthopedics, Windsor, CA (US)

( * ) Notice: Subject to any disclaimer, the term of this patent is extended or adjusted under 35 U.S.C. 154(b) by 30 days.

(21) Appl. No.: 14/594,006

(22) Filed: Jan. 9, 2015

(65) Prior Publication Data

US 2016/0199195 A1    Jul. 14, 2016

(51) Int. Cl.
*A61F 2/44* (2006.01)
*A61F 2/30* (2006.01)
*A61F 2/46* (2006.01)

(52) U.S. Cl.
CPC .......... *A61F 2/4455* (2013.01); *A61F 2/3094* (2013.01); *A61F 2/4611* (2013.01); *A61F 2002/30092* (2013.01); *A61F 2002/3093* (2013.01); *A61F 2002/30131* (2013.01); *A61F 2002/30156* (2013.01); *A61F 2002/30487* (2013.01); *A61F 2002/30537* (2013.01); *A61F 2002/30556* (2013.01); *A61F 2002/30579* (2013.01); *A61F 2002/30604* (2013.01); *A61F 2002/30785* (2013.01); *A61F 2002/4415* (2013.01); *A61F 2002/4475* (2013.01); *A61F 2002/4485* (2013.01); *A61F 2310/00359* (2013.01)

(58) Field of Classification Search
CPC ........ A61F 2/44; A61F 2/4455; A61F 2/4465; A61F 2/447; A61F 2002/4415; A61F 2002/4475; A61F 2002/30039; A61F 2002/448; A61F 2002/4485; A61F 2002/30092; A61F 2002/30093; A61F 2002/30095; A61F 2002/30097; A61F 2250/0042; A61F 2/4611; A61B 1/0058
See application file for complete search history.

(56) References Cited

U.S. PATENT DOCUMENTS 4,776,844 A  * 10/1988  Ueda .......................... 604/95.05
4,846,573 A  *  7/1989  Taylor et al. .............. 356/241.4
(Continued)

FOREIGN PATENT DOCUMENTS

IL  WO 2014033651 A1 *  3/2014  ............. A61F 2/442
WO       2006072941 A2      7/2006

*Primary Examiner* — Matthew Lawson
*Assistant Examiner* — Amy Sipp
(74) *Attorney, Agent, or Firm* — Robert Crownover

(57) ABSTRACT

A spinal fusion system method and apparatus can include: providing segments including a first segment and a second segment; and coupling the first segment to the second segment with a flexible member, the flexible member configured to have a deformable state based upon a temperature of the flexible member being below a transition temperature range or based upon a stress being applied to the flexible member, and the flexible member configured to enter a shape-set state from the deformable state based on the temperature of the flexible member rising above the transition temperature range, or based upon the stress being removed from the flexible member and the temperature of the flexible member being above the transition temperature range.

22 Claims, 9 Drawing Sheets

(56) References Cited

U.S. PATENT DOCUMENTS

| | | | |
|---|---|---|---|
| 5,716,416 A | 2/1998 | Lin | |
| 5,919,235 A | 7/1999 | Husson et al. | |
| 5,986,169 A | 11/1999 | Gjunter | |
| 6,127,597 A | 10/2000 | Beyar et al. | |
| 6,387,130 B1* | 5/2002 | Stone et al. | 623/17.16 |
| 7,604,870 B2 | 10/2009 | Chernyshov et al. | |
| 7,666,227 B2 | 2/2010 | Schaller | |
| 7,938,860 B2 | 5/2011 | Trieu | |
| 8,021,429 B2 | 9/2011 | Viker | |
| 8,034,110 B2 | 10/2011 | Garner et al. | |
| 8,206,423 B2 | 6/2012 | Siegal | |
| 8,328,812 B2* | 12/2012 | Siegal et al. | 606/83 |
| 8,366,773 B2 | 2/2013 | Schaller et al. | |
| 8,470,043 B2 | 6/2013 | Schaller et al. | |
| 8,486,109 B2 | 7/2013 | Siegal | |
| 8,518,117 B2 | 8/2013 | Sack et al. | |
| 8,556,978 B2 | 10/2013 | Schaller | |
| 8,579,983 B2 | 11/2013 | Garner et al. | |
| 8,591,583 B2 | 11/2013 | Schaller et al. | |
| 8,986,388 B2* | 3/2015 | Siegal et al. | 623/17.16 |
| 2002/0109986 A1 | 8/2002 | Siegel | |
| 2003/0055505 A1 | 3/2003 | Sicotte et al. | |
| 2004/0230309 A1 | 11/2004 | DiMauro et al. | |
| 2006/0189999 A1* | 8/2006 | Zwirkoski | 606/90 |
| 2006/0190083 A1* | 8/2006 | Arnin | A61F 2/442 623/17.13 |
| 2007/0067035 A1* | 3/2007 | Falahee | A61F 2/4455 623/17.11 |
| 2008/0009944 A1 | 1/2008 | McGuckin, Jr. | |
| 2008/0125865 A1* | 5/2008 | Abdelgany | A61F 2/447 623/17.16 |
| 2008/0133012 A1* | 6/2008 | McGuckin | 623/17.12 |
| 2008/0221687 A1 | 9/2008 | Viker | |
| 2008/0249628 A1* | 10/2008 | Altarac | A61F 2/4455 623/17.16 |
| 2009/0177207 A1 | 7/2009 | Schaller | |
| 2010/0114107 A1 | 5/2010 | Trieu | |
| 2011/0009969 A1* | 1/2011 | Puno | A61B 17/1757 623/17.12 |
| 2011/0046740 A1* | 2/2011 | Chen | A61F 2/4455 623/17.16 |
| 2011/0066192 A1* | 3/2011 | Frasier et al. | 606/86 A |
| 2011/0213463 A1 | 9/2011 | Kuslich | |
| 2011/0230967 A1 | 9/2011 | O'Halloran et al. | |
| 2011/0245924 A1 | 10/2011 | Kuslich | |
| 2011/0245926 A1* | 10/2011 | Kitchen | 623/17.16 |
| 2011/0307064 A1 | 12/2011 | Schaller | |
| 2012/0029643 A1 | 2/2012 | Robinson | |
| 2012/0071980 A1 | 3/2012 | Purcell et al. | |
| 2012/0123554 A1 | 5/2012 | Fonte | |
| 2012/0330314 A1 | 12/2012 | Schaller et al. | |
| 2013/0131810 A1 | 5/2013 | Schaller et al. | |
| 2013/0190880 A1 | 7/2013 | Schaller | |
| 2013/0226187 A1 | 8/2013 | Schaller et al. | |
| 2013/0282062 A1 | 10/2013 | McGrath et al. | |
| 2014/0025171 A1 | 1/2014 | Schaller | |
| 2014/0277481 A1* | 9/2014 | Lee | A61F 2/4455 623/17.16 |
| 2016/0074174 A1* | 3/2016 | Halverson | A61F 2/4455 623/17.11 |

* cited by examiner

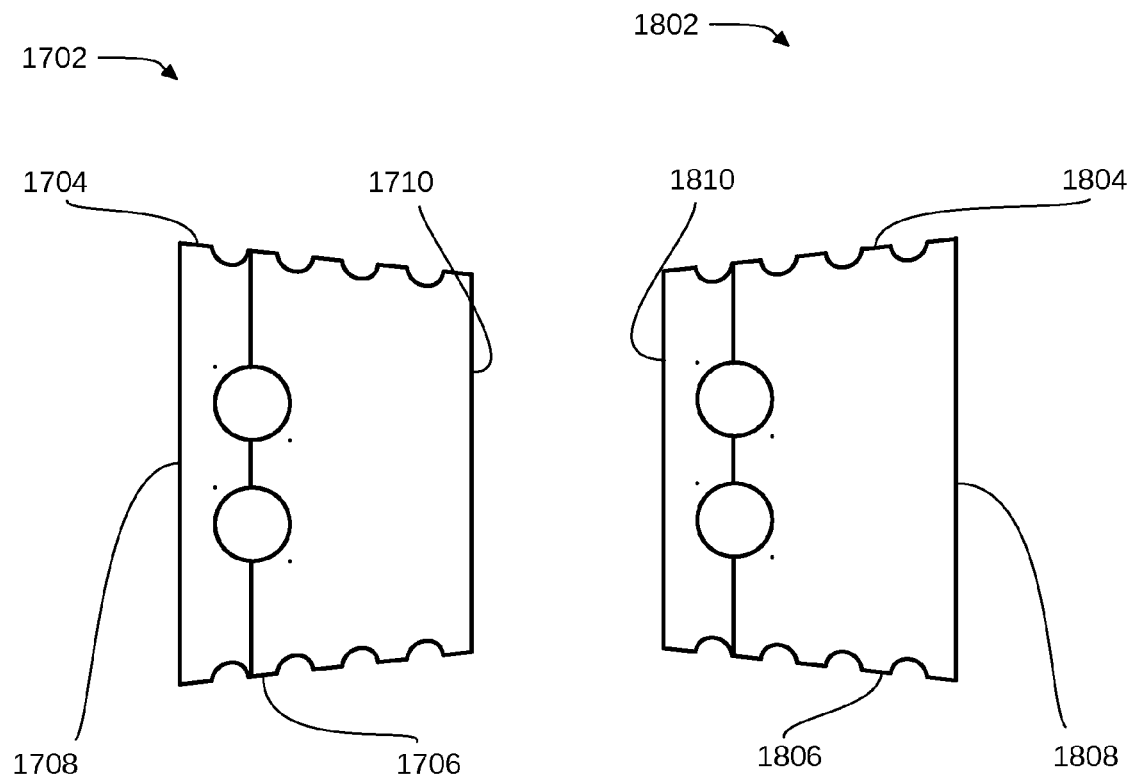
FIG. 17
FIG. 18
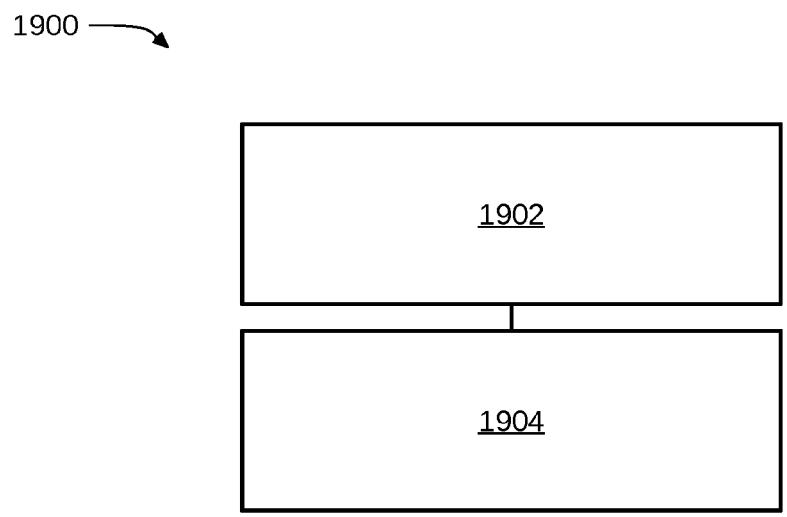
FIG. 19

SHAPE-MEMORY SPINAL FUSION SYSTEM

TECHNICAL FIELD

This disclosure relates to inter-body fusion systems, more particularly to inter-body fusion systems employing shape-memory materials.

BACKGROUND

Spinal fusion is sometimes necessary for patients having lumbar degenerative disc disease. It has been estimated that at least thirty percent of people aged thirty to fifty will have some degree of disc space degeneration, although not all will have pain or ever be diagnosed formally with degenerative disc disease. After a patient reaches sixty, it is more normal than not to have some level of disc degeneration.

A twisting injury often starts degenerative disc diseases, but it can also be initiated by every day wear and tear on the spine. Lower back pain is the most common symptom of a compromised disc emblematic of degenerative disc diseases. For most patients with lumbar degenerative disc disease, the pain is for the most part tolerable and low-grade, but continuous with occasional flaring of intense pain.

Pain can be simply centered on the lower back, or it can radiate to the hips and legs. It can get worse by sitting, or it can be intensified by twisting, lifting, or bending. For some, the pain from the disease decreases over time, since a fully degenerated disc has no pain-causing inflammatory proteins, and the disc usually collapses into a stable position-eliminating the micro-motion that often generates the pain.

Stabilization of vertebrae relative to each other, by implanting inter-body fusion devices, is a well-accepted surgical technique and has increasingly been used to correct for degenerative disc disease. The implantation of internal fusion devices can often be traumatic. If insufficient stabilization or incorrect anatomical alignment occurs, then revision surgery or on-going pain may be experienced by the patient.

Many variations of this basic surgical technique exist but often require considerable time and effort for successful implant placement. This is frequently due to the fact that such systems typically require both excessive surgical tissue dissection and mechanical vertebral distraction such that the various stabilization components of the system can be successfully positioned in a patient's intervertebral space.

In addition, dimensional constraints typically imposed by access considerations are often in conflict with the desire to place the largest implant possible having an effective anatomical shape to support the loads transmitted across the vertebral endplates. Specifically, the larger and more curved the implant inserted, the greater the amount of resulting tissue damage both in the intervertebral space, and in the surrounding tissues. There is therefore a need for devices for introduction into a body in a substantially straight configuration and to form a predefined curved configuration, to reduce time, to reduce effort, and to reduce tissue damage.

Solutions have been long sought but prior developments have not taught or suggested any complete solutions, and solutions to these problems have long eluded those skilled in the art. Thus a considerable need still remains.

SUMMARY

A spinal fusion system apparatus and methods, providing introduction into a body in a substantially straight configuration and thereafter to form a predefined curved configuration, to reduce time, to reduce effort, and to reduce tissue damage, are disclosed. The spinal fusion system can include: segments including a first segment and a second segment; and the first segment coupled to the second segment with a flexible member, the flexible member configured to have a deformable state based upon a temperature of the flexible member being below a transition temperature range or based upon a stress being applied to the flexible member, and the flexible member configured to enter a shape-set state from the deformable state based on the temperature of the flexible member rising above the transition temperature range, or based upon the stress being removed from the flexible member and the temperature of the flexible member being above the transition temperature range.

It is disclosed that, in some embodiments, the segments can include ridges; tapered surfaces on a top side or a bottom side reducing the height of the segment; an angled surface to compensate for a lordotic angle or kyphotic angle; and a cavity filled with an osteogenic material. It is further disclosed that, in some embodiments, the segments can include a height fixation extension mated to a height fixation receptacle and configured to lock the top portion and the bottom portion in a distracted state.

It is disclosed that, in some embodiments, the flexible member can couple the segments through a conduit; and that the transition temperature range of the flexible member can include an austenite finish temperature and a martensite finish temperature and that the shape-set state can be an austenite state and that the deformable state can be a martensite state. It is further disclosed that, in some embodiments, the flexible member is configured to have a martensite state based upon the temperature of the flexible member being below a martensite finish temperature or based upon stress being applied to the flexible member, and the flexible member configured to enter an austenite state from the martensite state based on the temperature of the flexible member rising above an austenite finish temperature, or based upon the stress being removed from the flexible member and the temperature of the flexible member being above the austenite finish temperature.

It is disclosed that, in some embodiments, the flexible member is shape-set to have a curved shape; the austenite finish temperature below thirty-seven degrees Celsius; an insertion guide is coupled to the first segment and the second segment, and the insertion guide configured to maintain the flexible member in the martensite state and the first segment and the second segment in a straight configuration.

Accordingly, it has been discovered that one or more embodiments described herein provide a spinal fusion system apparatus and methods allowing introduction into a body in a substantially straight configuration and thereafter to form a predefined curved configuration, while simultaneously reducing time, effort, and tissue damage, during a spinal fusion procedure.

Other contemplated embodiments can include objects, features, aspects, and advantages in addition to or in place of those mentioned above. These objects, features, aspects, and advantages of the embodiments will become more apparent from the following detailed description, along with the accompanying drawings.

BRIEF DESCRIPTION OF THE DRAWINGS

The spinal fusion system is illustrated in the figures of the accompanying drawings which are meant to be exemplary and not limiting, in which like reference numerals are intended to refer to like components, and in which:

FIG. 17 is a side view of a segment in a fifth embodiment.

FIG. 18 is a side view of a segment in a sixth embodiment.

FIG. 19 is a block diagram for a method of manufacturing a spinal fusion system.

DETAILED DESCRIPTION

Figure 1:
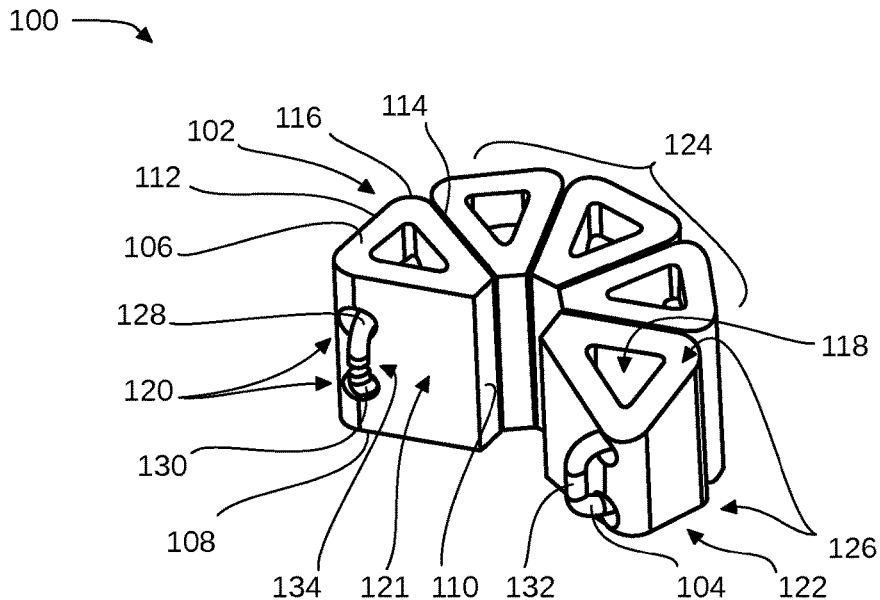
FIG. 1 is an isometric view of a spinal fusion system in a first embodiment in a shape-set configuration.

In the following description, reference is made to the accompanying drawings that form a part hereof, and in which are shown by way of illustration, embodiments in which the spinal fusion system may be practiced. It is to be understood that other embodiments may be utilized and structural changes may be made without departing from the scope of the spinal fusion system.

The spinal fusion system is described in sufficient detail to enable those skilled in the art to make and use the spinal fusion system and provide numerous specific details to give a thorough understanding of the spinal fusion system; however, it will be apparent that the spinal fusion system may be practiced without these specific details.

In order to avoid obscuring the spinal fusion system, some well-known system configurations are not disclosed in detail. Likewise, the drawings showing embodiments of the system are semi-diagrammatic and not to scale and, particularly, some of the dimensions are for the clarity of presentation and are shown greatly exaggerated in the drawing FIGs. Generally, the spinal fusion system can be operated in any orientation.

As used herein, the term system is defined as a device or method depending on the context in which it is used. For expository purposes, the term "horizontal", as used herein, is defined as a plane parallel to the top plane or surface of the terminal segment, regardless of its orientation. The term "vertical" refers to a direction perpendicular to the horizontal as just defined. Terms, such as "above", "below", "bottom", "top", "side", "higher", "lower", "upper", "over", and "under", are defined with respect to the horizontal plane. The term coupled, as used herein, is defined as a physical connection whether direct or indirect.

Referring now to FIG. 1, therein is shown an isometric view of a spinal fusion system 100 in a first embodiment in a shape-set configuration. The spinal fusion system 100 is depicted in this first embodiment having segments 102 coupled with a flexible member 104.

The segments 102 are shown having top sides 106, bottom sides 108, radially inner sides 110, and radially outer sides 112. The segments 102 further include radially oriented sides 114. The radially oriented sides 114 can extend from the radially inner sides 110 out toward the radially outer sides 112.

Rounded corners 116 can connect the radially oriented sides 114 with the radially outer sides 112. The radially inner sides 110, the radially outer sides 112, and the radially oriented sides 114 can form a generally trapezoidal shape with the radially inner sides 110 and the radially outer sides 112 parallel on each of the segments 102. In an alternative contemplated embodiment, the radially outer sides 112 and the radially inner sides 110 can be curved.

The shape-set configuration of the spinal fusion system 100 is shown with the segments 102 arranged in an arc around a center point. The radially oriented sides 114 are depicted extending out from the radially inner sides 110 and away from a center point of the arc.

The radially oriented sides 114 are further depicted in direct contact with the radially oriented sides 114 of the adjacent segments 102. The radially inner sides 110 are shown nearer the center point while the radially outer sides 112 are shown further from the center point.

The segments 102 are further shown having cavities 118 and conduits 120. It is contemplated that the cavities 118 can be used to hold osteogenic material to accelerate the fusion process. It is contemplated that the osteogenic material can include natural materials and synthetic materials such as bone graft, bone morphogenetic proteins, calcium phosphates, calcium sulphate, or a combination thereof.

The conduits 120 can provide a channel for the flexible member 104 to traverse through each of the segments 102. It is contemplated that the conduits 120 can be arranged vertically in two channels. The conduits 120 of each of the segments 102 can be arranged to open near the conduits 120 of each adjacent segment 102 enabling the flexible member 104 to pass through each of the segments 102 and into the adjacent segment 102.

The conduits 120 are depicted positioned nearer the radially outer sides 112 traversing through a portion of the radially oriented sides 114 and the rounded corners 116 on of each of the segments 102. The flexible member 104 is depicted extending through the conduits 120 into the cavities 118 of the segments 102 and out of a terminal segment 121 and out of a leading segment 122.

The terminal segment 121 and the leading segment 122 can be end segments of the spinal fusion system 100. The leading segment 122 can be the initial segment inserted during a spinal fusion procedure while the terminal segment 121 can be the last segment inserted during a spinal fusion procedure.

Between the terminal segment 121 and the leading segment 122 are intermediary segments 124. The leading segment 122 is depicted to include tapered surfaces 126. In the present embodiment, the tapered surfaces 126 are shown on the top sides 106 and the bottom sides 108 of the leading segment 122.

The tapered surfaces 126 are shown angling down from the top sides 106 and the bottom sides 108 of the intermediary segment 124 immediately adjacent to the leading segment 122 toward the conduits 120 of the leading segment 122. It is contemplated that only a portion of the top sides 106 and bottom sides 108 of the leading segment 122 could include the tapered surfaces 126.

It is further contemplated that portions of the top sides 106 and the bottom sides 108 of the intermediary segments 124 could also include the tapered surfaces 126. The tapered surfaces 126 are depicted as flat and angular; however, the tapered surfaces 126 can be rounded.

The tapered surfaces 126 can provide a means to distract or increase the distance between adjacent vertebrae during a spinal fusion procedure without requiring additional distraction tools. It is further contemplated that some of the top sides 106 or the bottom sides 108 of the segments 102 can be angled to compensate for the lordotic angle or the kyphotic angle of the spine of the patient having the fusion procedure performed.

The segments 102 can be made of a radiolucent material such as Polyether ether ketone or carbon fiber. The segments 102 can further be made of an osteogenic material such as allograft, autologous, or synthetic. The segments 102 can further be made of a radiopaque material such as titanium, stainless steel, cobalt chrome, silicon nitride, porous nitinol, porous titanium, or porous tantalum.

The flexible member 104 can connect the segments 102 together through the conduits 120 and can maintain the shape-set configuration of the segments 102. The flexible member 104 is depicted formed in rod or wire extending through the segments 102.

It is contemplated the flexible member 104 could be formed as a sheet, wire, strip, tube, or a combination thereof. The flexible member 104 can include an upper arm 128 extending through an upper one of the conduits 120 in each of the segments 102. The flexible member 104 can further include a lower arm 130 extending through a bottom one of the conduits 120 in each of the segments 102.

The upper arm 128 and the lower arm 130 can meet and can be coupled or joined at a looped end 132. The looped end 132 can be positioned near the leading segment 122 and can connect the upper arm 128 and the lower arm 130 of the flexible member 104 through the conduits 120 in the radially oriented sides 114 and rounded corners 116 of the leading segment 122.

The flexible member 104 can further include an open end 134 where the upper arm 128 and the lower arm 130 are not coupled or connected but remain spaced apart. The open end 134 can include curved portions of the upper arm 128 and lower arm 130 that extend out of the conduits 120 of the terminal segment 121. It is contemplated that the open end 134 could be connected by welding, or threaded connections.

The flexible member 104 is contemplated to be made of a shape-memory material such as an alloy of copper-aluminum-nickel; nickel-titanium; or zinc, copper, gold and iron. For descriptive clarity, the flexible member 104 is described with regard to Nitinol, an alloy of nickel and titanium.

In the present illustrative embodiment, the flexible member 104 is contemplated to possess both shape-memory and super elastic properties. Shape-memory properties of the flexible member 104 can be induced by shape-setting the flexible member 104.

The flexible member 104 can be shape-set by constraining the flexible member 104 in the shape-set configuration, such as an arc, then heat treating the flexible member 104 while in the shape-set configuration. It is contemplated that heat treating the flexible member 104 can include bringing the flexible member 104 to a high temperature, such as 400-550 degrees Celsius, and then rapidly cooling the flexible member 104.

The flexible member 104 can retain the shape-set configuration while the flexible member 104 is in a shape-set state. The shape-set state can be an austenite state.

Cooling the flexible member 104 below a transition temperature range can force the flexible member 104 to enter a deformable state. The deformable state can be a martensite state.

In a narrow temperature band near the transition temperature range the flexible member 104 can also be forced into the deformable state with stress. Forcing the flexible member 104 into the deformable state with stress will provide the super-elastic characteristics while forcing the flexible member 104 into the deformable state by lowering the temperature of the flexible member 104 will provide the shape-memory characteristics.

When the flexible member 104 is in the deformable state, the flexible member 104 can be deformed into a straight configuration shown below with regard to FIG. 2. The flexible member 104 can be placed back into the shape-set state by increasing the temperature of the flexible member 104 above the transition temperature range or removing the stress.

The flexible member 104 differs from other materials in that when the flexible member 104 is in the deformable state atomic planes within the flexible member 104 can be rearranged without causing slip, or permanent deformation. It has been found in some cases that the maximum amount of deformation in the deformable state that the shape-memory materials of the flexible member 104 can hold without permanent damage is up to eight percent for some alloys. This compares with a maximum strain one-half a percent for conventional steels.

The transition temperature range of the flexible member 104 can consist of four temperatures, those are a martensite start temperature, a martensite finish temperature, an austenite start temperature, and an austenite finish temperature. The martensite start temperature is the temperature when the flexible member 104 begins to change from the austenite state to the martensite state while the martensite finish temperature is the temperature when the flexible member 104 completes the transformation from the austenite state to the martensite state.

The austenite start temperature is the temperature when the flexible member 104 begins to change from the martensite state to the austenite state while the austenite finish temperature is the temperature when the flexible member 104 completes the transformation from the martensite state to the austenite state. It is contemplated that the austenite finish temperature should be below the body temperature of about thirty-seven degrees Celsius. In some embodiments, it is critical that the austenite finish temperature be below body temperature so that the flexible member 104 can be in the shape-set state after implantation in a human.

Figure 2:
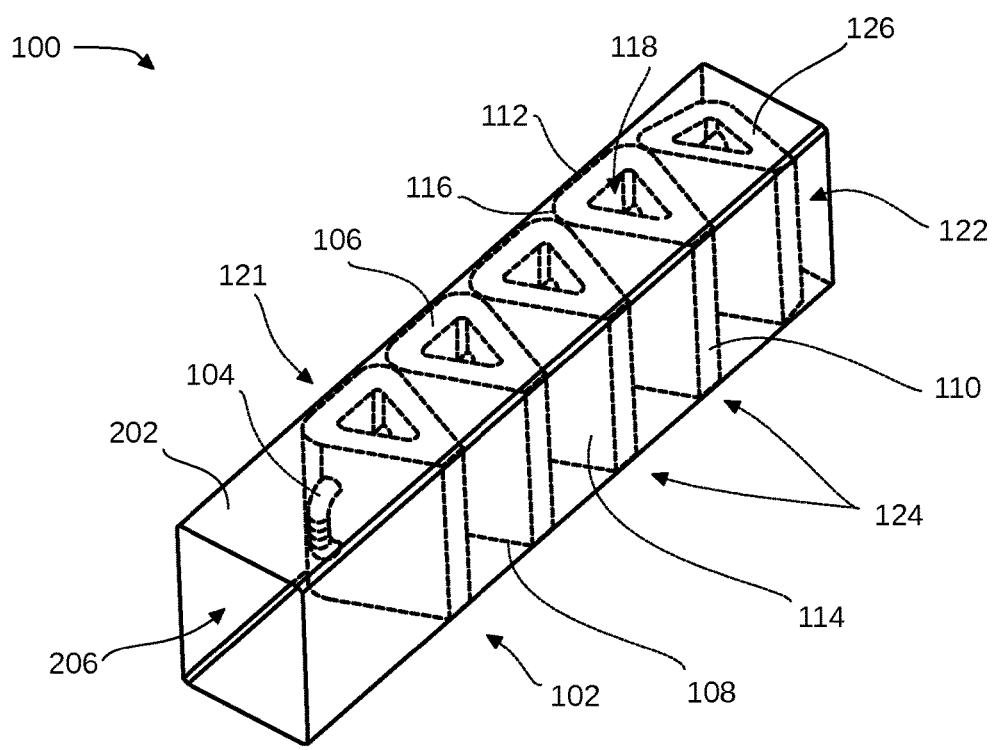
FIG. 2 is an isometric view of the spinal fusion system of FIG. 1 in a straight configuration.

It has been discovered that implementing the flexible member 104, coupling the segments 102 together, provides greatly increased ease of use during spinal fixation procedures because the flexible member 104 can be deformed into the straight configuration of FIG. 2 in a deformable state and then will return to the shape-set configuration without requiring external forces to be applied as the material itself supplies a restoring force during the transformation between the deformable state and the shape-set state.

It has further been discovered that implementing the tapered surfaces 126 of the segments 102 decreases the time and difficulty of performing the spinal fusion procedure because the tapered surfaces 126 can distract the vertebra as the segments 102 are inserted and can eliminate the need for additional tools.

Referring now to FIG. 2, therein is shown an isometric view of the spinal fusion system 100 of FIG. 1 in a straight configuration. The segments 102 are shown aligned in a straight row and contained within an insertion guide 202.

The insertion guide 202 is contemplated to maintain the flexible member 104 in the deformable state either from stress or temperature. The insertion guide 202 can be a conduit as shown in the present illustrative embodiment or a mandrel as is shown in the illustrative embodiment of FIG. 7.

The segments 102 within the insertion guide 202 are shown having the rounded corners 116 of the segments 102 in contact with the rounded corners 116 of the adjacent segments 102. It is contemplated that the rounded corners 116 can provide structural support for the segments 102 as the flexible member 104 transitions from the deformable state to the shape-set state.

In this way, the rounded corners 116 can provide a smooth transition and prevent slipping between the segments 102. The bottom sides 108, top sides 106, radially inner sides 110, and radially outer sides 112 of the terminal segment 121 and the intermediary segments 124 are depicted in contact with the insertion guide 202.

The radially inner sides 110 and the radially outer sides 112 of the leading segment 122 are shown in direct contact with the insertion guide 202. The top sides 106 and the bottom sides 108 of the leading segment 122 with the tapered surfaces 126 are not in contact with the insertion guide 202 but are suspended within the insertion guide 202.

It is contemplated that the insertion guide 202 can provide a sterile environment for safe transport and storage of the segments 102 and the flexible member 104. Further it is contemplated that the insertion guide 202 can be maintained at a temperature below the transition temperature range of the flexible member 104 to keep the flexible member 104 in the deformable state while in the insertion guide 202.

It is further contemplated that the insertion guide 202 can be maintained at a temperature below the transition temperature range of the flexible member 104 thereby maintaining the flexible member 104 in the deformable state until the flexible member 104 and the segments 102 are inserted during the spinal fusion procedure. It is contemplated that the cavities 118 of the segments 102 can include the osteogenic material while the segments 102 are within the insertion guide 202.

The insertion guide 202 provide compression on the segments 102. The compression provided by the insertion guide 202 can provide a secure fit for the segments 102 within the insertion guide 202 so that the segments 102 do not deteriorate with motion or impact. The compression provided by the insertion guide 202 can further provide the stress required to maintain the flexible member 104 within the deformable state for super-elasticity.

The insertion guide 202 can have openings 206 on each end of the insertion guide 202. The openings 206 near the terminal segment 121 can allow the spinal fusion system 100 to be inserted within the insertion guide 202, and the openings 206 of the insertion guide 202 near the leading segment 122 can be used to force or extrude the segments 102 out of the insertion guide 202. The openings 206 near the terminal segment 121 can also facilitate the loading of the segments 102 within the insertion guide 202. The openings 206 near the leading segment 122 can be used to direct the segments 102 between vertebrae during a spinal fusion procedure.

Figure 3:
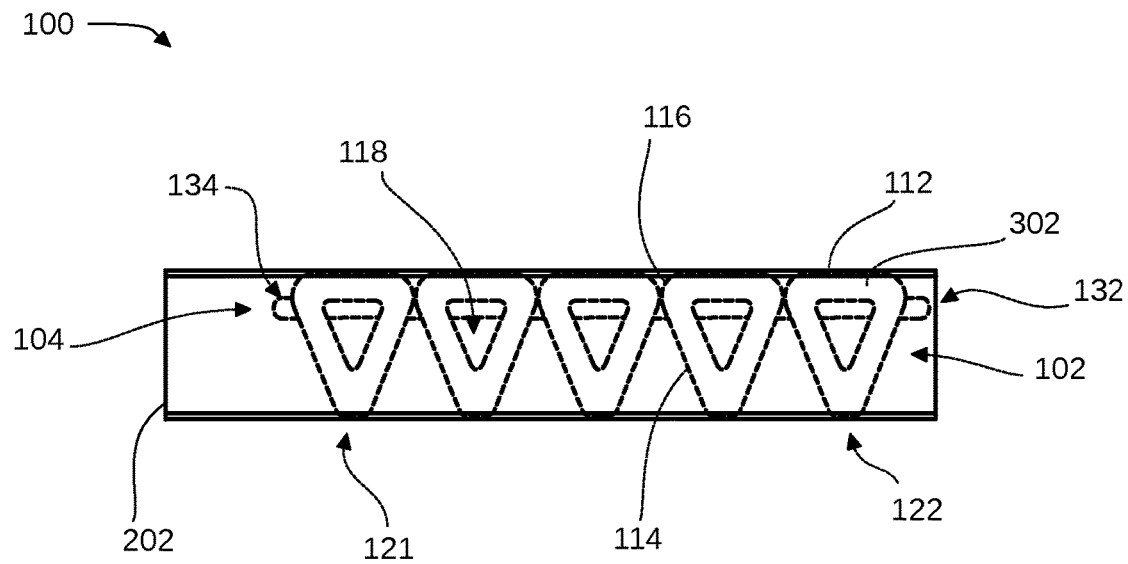
FIG. 3 is a top view of the spinal fusion system of FIG. 2.

Referring now to FIG. 3, therein is shown a top view of the spinal fusion system 100 of FIG. 2. The segments 102 and the flexible member 104 are shown within the insertion guide 202.

The flexible member 104 is depicted extending through the segments 102 and through the cavities 118 of the segments 102. The flexible member 104 is located near the radially outer sides 112 of the segments 102.

It is contemplated that the location of the flexible member 104 near the radially outer sides 112 can be located along a neutral axis, that is the open end 134 and the looped end 132 of the flexible member 104 can maintain the same distance from the terminal segment 121 and the leading segment 122 when the flexible member 104 is in the shape-set configuration as well as the straight configuration.

The segments 102 can include walls 302 that terminate in the radially oriented sides 114, radially inner sides 110, or the radially outer sides 112 and the cavities 118. The flexible member 104 is shown extending partially through the walls 302 of the segments 102 near the radially outer sides 112.

It is contemplated that the conduits 120 of FIG. 1 extending through the walls 302 of the segments 102, can provide extra guidance for the transition of the flexible member 104 between the deformable state and the shape-set state.

Figure 4:
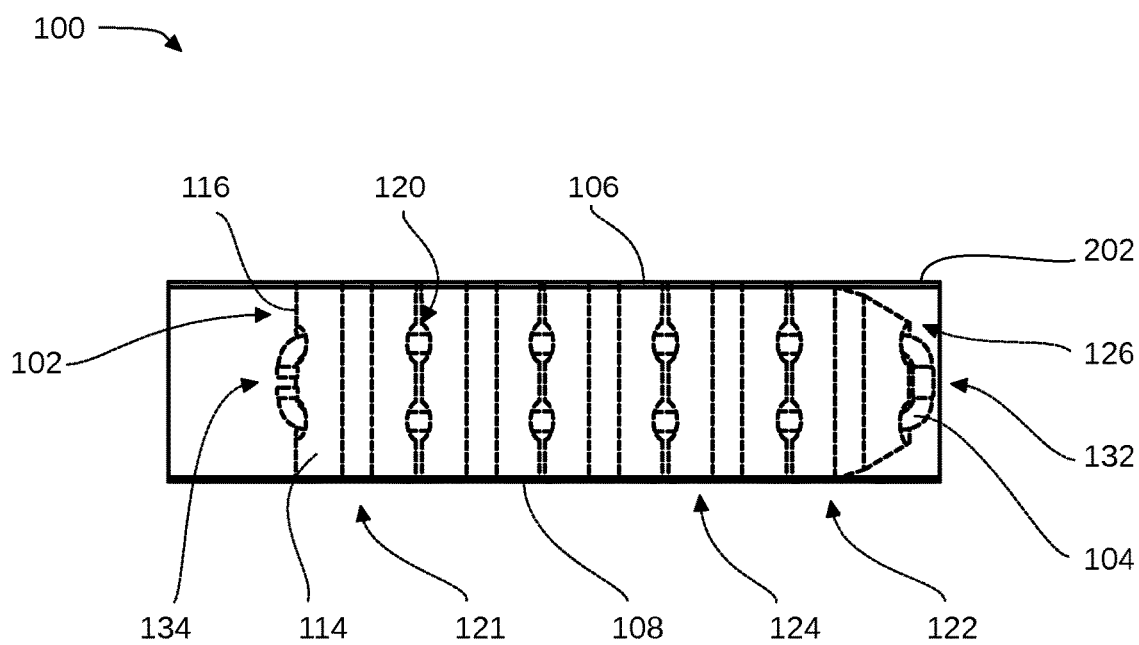
FIG. 4 is a side view of the spinal fusion system of FIG. 2.

Referring now to FIG. 4, therein is shown a side view of the spinal fusion system 100 of FIG. 2. The segments 102 and the flexible member 104 are shown contained within the insertion guide 202.

The top sides 106 and the bottom sides 108 of terminal segment 121 and the intermediary segments 124 are depicted in direct contact with the insertion guide 202. The top sides 106 and the bottom sides 108 of the leading segment 122 having the tapered surfaces 126 are not in contact with the insertion guide 202.

The flexible member 104 is shown extending through the conduits 120 of the segments 102. As the flexible member 104 extends from the conduits 120 of the leading segment 122, the flexible member 104 loops around forming the looped end 132.

The looped end 132 of the flexible member 104 can provide additional taper for the tapered surfaces 126 providing greater ease of insertion. The open end 134 of the flexible member 104 can be seen extending from the terminal segment 121.

The open end 134 and the looped end 132 can be curved and provide a compressive force to maintain contact between the segments 102. It is contemplated the flexible member 104 can be threaded through the conduits 120 of the segments 102 using the open end 134 to wrap around portions of the rounded corners 116 and the radially oriented sides 114 of the terminal segment 121.

Figure 5:
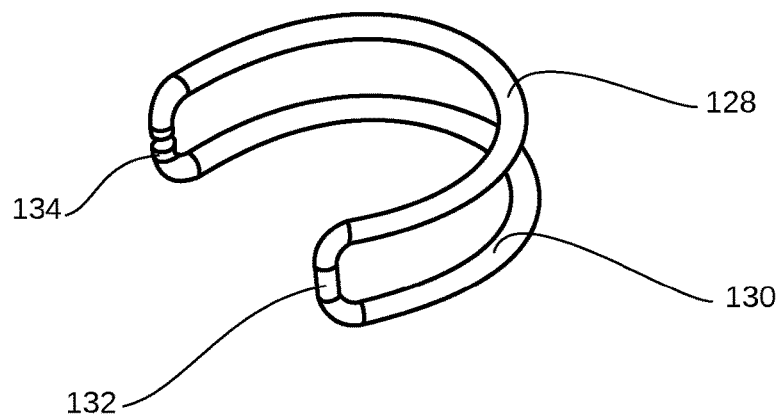
FIG. 5 is an isometric view of the shape-memory member of FIG. 1.

Referring now to FIG. 5, therein is shown an isometric view of the shape-memory member of FIG. 1. The flexible member 104 is shown having the upper arm 128 and the lower arm 130 in the shape-set configuration.

The shape-set configuration is depicted as an arc but it is contemplated that the shape-set configuration of the flexible member 104 could include other shapes. The open end 134 and the looped end 132 are shown curving between the upper arm 128 and the lower arm 130. The upper arm 128 and the lower arm 130 are depicted with a constant distance therebetween and with an identical shape.

It is contemplated that the looped end 132 and the open end 134 could be made of different material that does not enter the deformable state when the upper arm 128 and lower arm 130 enter the deformable state. Providing the looped end 132 and the open end 134 of different material than the upper arm 128 and the lower arm 130 can maintain the distance between the upper arm 128 and the lower arm 130 when the flexible member 104 is in the deformable state. The open end 134 and the looped end 132 are depicted having the same cross-sectional area as the upper arm 128 and the lower arm 130.

Figure 6:
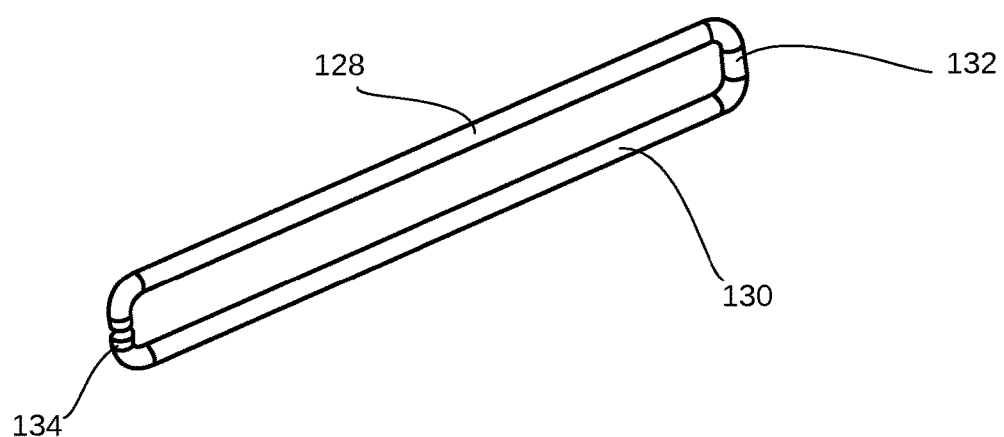
FIG. 6 is an isometric view of the shape-memory member of FIG. 2.

Referring now to FIG. 6, therein is shown an isometric view of the shape-memory member of FIG. 2. The flexible member 104 is shown having the upper arm 128 and the lower arm 130 in the straight configuration.

The straight configuration is depicted as having the upper arm 128 and the lower arm 130 in parallel linear arrangement. The upper arm 128 and the lower arm 130 are further depicted with a constant distance therebetween and an identical shape. The open end 134 and the looped end 132 are shown curving between the upper arm 128 and the lower arm 130.

It is contemplated that the looped end 132 and the open end 134 could be made of different material that does not enter the deformable state when the upper arm 128 and lower arm 130 enter the deformable state. Providing the looped end 132 and the open end 134 of different material than the upper arm 128 and the lower arm 130 can maintain the distance between the upper arm 128 and the lower arm 130 when the flexible member 104 is in the deformable state. The open end 134 and the looped end 132 are depicted having the same cross-sectional area as the upper arm 128 and the lower arm 130.

Figure 7:
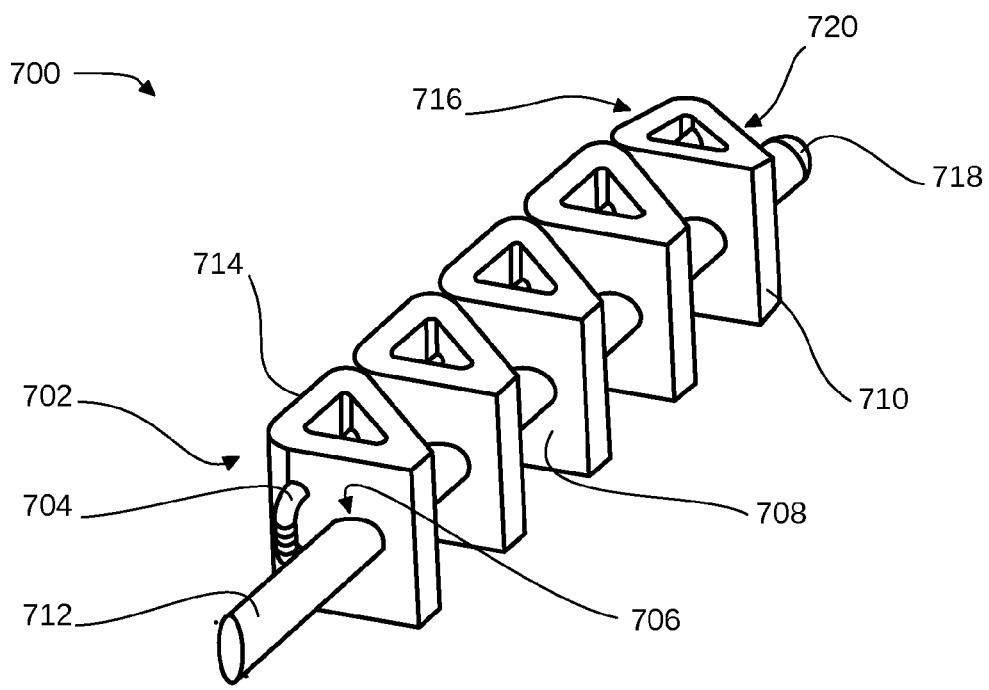
FIG. 7 is an isometric view of a spinal fusion system in a second embodiment in a straight configuration.

Referring now to FIG. 7, therein is shown an isometric view of a spinal fusion system 700 in a second embodiment in a straight configuration. The spinal fusion system 700 is shown having segments 702 aligned in a straight row and coupled together with a flexible member 704.

The flexible member 704 and the segments 702 are contemplated to be similar to those of FIG. 1 with the exception of an insertion guide hole 706 extending through the segments 702. The insertion guide hole 706 is depicted extending through radially oriented sides 708 and nearer to radially inner sides 710 than the flexible member 704.

The segments 702 are depicted having an insertion guide 712 extending through the insertion guide hole 706 and between the segments 702. The insertion guide 712 is contemplated to maintain a flexible member 704 in the deformable state by keeping the flexible member 704 under stress.

The insertion guide 712 can be a mandrel as shown in the present illustrative embodiment or a conduit as is shown in the illustrative embodiment of FIG. 2. The insertion guide 712 can extend out of the radially oriented sides 708 of a leading segment 716 and terminate in a rounded tip 718. The rounded tip 718 is depicted as extended beyond the leading segment 716.

The rounded tip 718 of the insertion guide 712 can aid in the distraction of the vertebra during a spinal fusion procedure. The insertion guide 712 is shown having a smaller cross-section than the narrowest portion of tapered surfaces 720 on the leading segment 716.

In other embodiments it is contemplated that the narrowest area of the tapered surfaces 720 could be similar in cross-section as the insertion guide 712 and that an angle of the rounded tip 718 could blend into an angle of the tapered surfaces 720. The insertion guide 712 is shown extending linearly through the segments 702 however it is contemplated that the insertion guide 712 could be curved to a degree less than the shape-set configuration so as to maintain the flexible member 704 in the deformable state.

Figure 8:
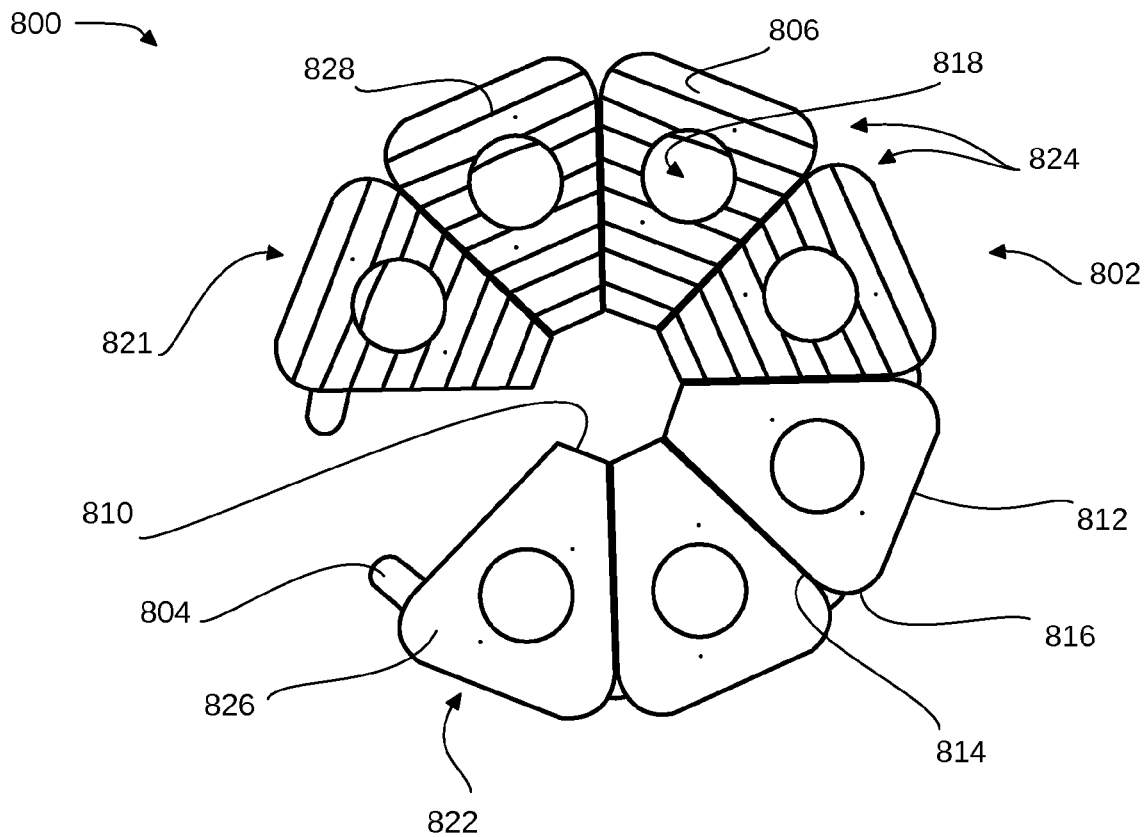
FIG. 8 is a top view of a spinal fusion system in a third embodiment in a shape-set configuration.

Referring now to FIG. 8, therein is shown a top view of a spinal fusion system 800 in a third embodiment in a shape-set configuration. The spinal fusion system 800 is depicted in this third embodiment having segments 802 coupled with a flexible member 804.

The segments 802 are shown having top sides 806, radially inner sides 810, and radially outer sides 812. The segments 802 further include radially oriented sides 814. The radially oriented sides 814 can extend from the radially inner sides 810 out toward the radially outer sides 812.

Rounded corners 816 can connect the radially oriented sides 814 with the radially outer sides 812. The radially inner sides 810, the radially outer sides 812, and the radially oriented sides 814 can form a generally trapezoidal shape with the radially inner sides 810 and the radially outer sides 812 parallel on each of the segments 802. In an alternative contemplated embodiment, the radially outer sides 812 and the radially inner sides 810 can be curved.

The shape-set configuration of the spinal fusion system 800 is shown with the segments 802 arranged in an arc around a center point. The radially oriented sides 814 are depicted extending out from the radially inner sides 810 and away from a center point of the arc. The radially inner sides 810 are depicted as sides of the segments 802 located closer to a center of the arc than the radially outer sides 812 of the segments 802 based on the segments 802 being in a curved shape-set configuration, and the radially inner sides 810 having a shorter length than the radially outer sides 812.

The radially oriented sides 814 are further depicted in direct contact with the radially oriented sides 814 of the adjacent segments 802. The radially inner sides 810 are shown nearer the center point while the radially outer sides 812 are shown further from the center point.

The segments 802 are further shown having cavities 818. It is contemplated that the cavities 818 can be used to hold osteogenic material to accelerate the fusion process. It is contemplated that the osteogenic material can include natural materials and synthetic materials such as bone graft, calcium phosphates, bone morphogenetic proteins, calcium sulphate, or a combination thereof.

The cavities 818 are depicted extending entirely through the segments 802 as circular holes. In other contemplated embodiments, the cavities 818 can extend only partially through the segments 802.

The flexible member 804 is depicted extending through the segments 802 and into the cavities 818 of the segments 802. The flexible member 804 is depicted extending out of a terminal segment 821 and out of a leading segment 822.

The terminal segment 821 and the leading segment 822 can be end segments of the spinal fusion system 800. The leading segment 822 can be the initial segment inserted during a spinal fusion procedure while the terminal segment 821 can be the last segment inserted during a spinal fusion procedure.

Between the terminal segment 821 and the leading segment 822 are intermediary segments 824. The leading segment 822 is depicted to include tapered surfaces 826. In the present embodiment, the tapered surfaces 826 are shown on the top sides 806 of the leading segment 822 and the next two adjacent intermediary segments 824.

The tapered surfaces 826 can angle down from near the top side 806 of the third intermediary segment 824 from the leading segment 822 toward the flexible member 804. The tapered surfaces 826 are depicted as flat and angular; however, the tapered surfaces 826 can be rounded.

The tapered surfaces 826 can provide a means to distract or increase the distance between adjacent vertebrae during a spinal fusion procedure without requiring additional distraction tools. The segments 802 can be made of a radiolucent material such as Polyether ether ketone or carbon fiber. The segments 802 can further be made of an osteogenic material such as allograft, autologous, or synthetic. The segments 802 can further be made of a radiopaque material such as titanium, stainless steel, cobalt chrome, silicon nitride, porous nitinol, porous titanium, or porous tantalum.

The terminal segment 821 and three of the intermediary segments 824 next to the terminal segment 821 include ridges 828 on the top sides 806. The ridges 828 can minimize migration of the segments 802 when the segments 802 are implanted between vertebrae during a spinal fusion procedure.

The ridges 828 are depicted as extending across the top sides 806 parallel to the radially outer sides 812 and the radially inner sides 810. The flexible member 804 can connect the segments 802 together and can maintain the shape-set configuration of the segments 802. The flexible member 804 is depicted formed in rod or wire extending through the segments 802.

It is contemplated the flexible member 804 could be formed as a sheet, wire, strip, tube, or a combination thereof. The flexible member 804 is contemplated to be made of a shape-memory material such as an alloy of copper-aluminum-nickel; nickel-titanium; or zinc, copper, gold and iron. For descriptive clarity, the flexible member 804 is described with regard to Nitinol, an alloy of nickel and titanium.

In the present illustrative embodiment, the flexible member 804 is contemplated to possess both shape-memory and super elastic properties. Shape-memory properties of the flexible member 804 can be induced by shape-setting the flexible member 804.

The flexible member 804 can be shape-set by constraining the flexible member 804 in the shape-set configuration, such as an arc, then heat treating the flexible member 804 while in the shape-set configuration. It is contemplated that heat treating the flexible member 804 can include bringing the flexible member 804 to a high temperature, such as 400-550 degrees Celsius, and then rapidly cooling the flexible member 804.

The flexible member 804 can retain the shape-set configuration while the flexible member 804 is in a shape-set state. The shape-set state can be an austenite state.

Cooling the flexible member 804 below a transition temperature range can force the flexible member 804 to enter a deformable state. The deformable state can be a martensite state.

In a narrow temperature band near the transition temperature range the flexible member 804 can also be forced into the deformable state with stress. Forcing the flexible member 804 into the deformable state with stress will provide the super-elastic characteristics while forcing the flexible member 804 into the deformable state by lowering the temperature of the flexible member 804 will provide the shape-memory characteristics.

When the flexible member 804 is in the deformable state, the flexible member 804 can be deformed into a straight configuration shown below with regard to FIG. 9. The flexible member 804 can be placed back into the shape-set state by increasing the temperature of the flexible member 804 above the transition temperature range or removing the stress.

The flexible member 804 differs from other materials in that when the flexible member 804 is in the deformable state atomic planes within the flexible member 804 can be rearranged without causing slip, or permanent deformation. It has been found in some cases that the maximum amount of deformation in the deformable state that the shape-memory materials of the flexible member 804 can hold without permanent damage is up to eight percent for some alloys. This compares with a maximum strain one-half a percent for conventional steels.

The transition temperature range of the flexible member 804 can consist of four temperatures, those are a martensite start temperature, a martensite finish temperature, an austenite start temperature, and an austenite finish temperature. The martensite start temperature is the temperature when the flexible member 804 begins to change from the austenite state to the martensite state while the martensite finish temperature is the temperature when the flexible member 804 completes the transformation from the austenite state to the martensite state.

The austenite start temperature is the temperature when the flexible member 804 begins to change from the martensite state to the austenite state while the austenite finish temperature is the temperature when the flexible member 804 completes the transformation from the martensite state to the austenite state. It is contemplated that the austenite finish temperature should be below the body temperature of about thirty-seven degrees Celsius.

Figure 9:
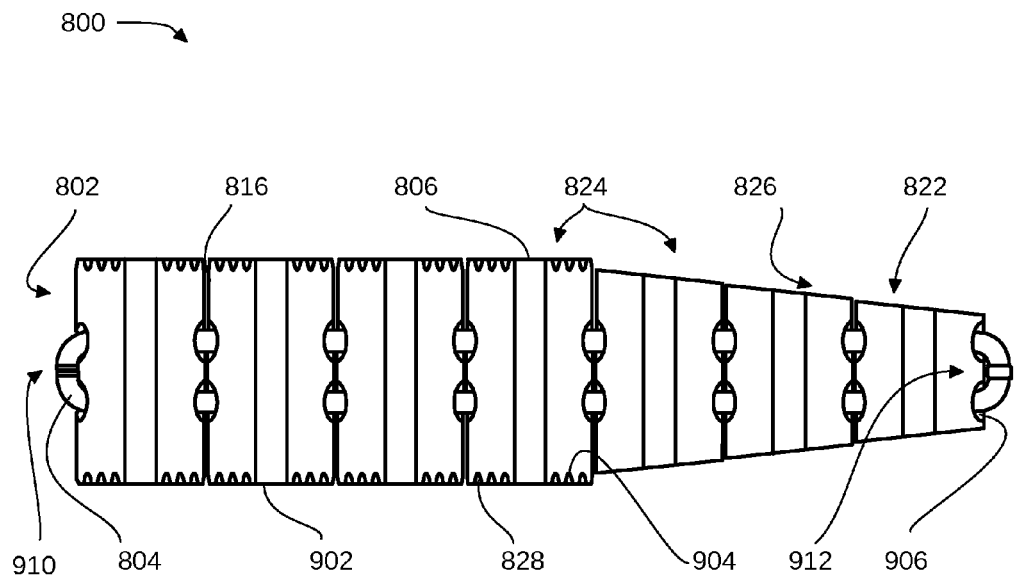
FIG. 9 is a side view of the spinal fusion system of FIG. 8 in a straight configuration.

It has been discovered that implementing the flexible member 804, coupling the segments 802 together, provides greatly increased ease of use during spinal fixation procedures because the flexible member 804 can be deformed into the straight configuration of FIG. 9 in a deformable state and then will return to the shape-set configuration without requiring external forces to be applied as the material itself supplies a restoring force during the transformation between the deformable state and the shape-set state.

It has further been discovered that implementing the tapered surfaces 826 of the segments 802 decreases the time and difficulty of performing the spinal fusion procedure because the tapered surfaces 826 can distract the vertebra as the segments 802 are inserted and can eliminate the need for additional tools.

Referring now to FIG. 9, therein is shown a side view of the spinal fusion system 800 of FIG. 8 in a straight configuration. The segments 802 are shown aligned in a straight row with the flexible member 804 extending through the segments 802.

The flexible member 804 can be in the deformable state below the transition temperature range. When in this state, the flexible member 804 will maintain the straight configuration of the deformable state. Once the temperature of the flexible member 804 increases above the transition temperature range the flexible member 804 will move into the shape-set configuration of FIG. 8 depicted as an arc.

The segments 802 are shown having the rounded corners 816 of the segments 802 in contact with the rounded corners 816 of the adjacent segments 802. It is contemplated that the rounded corners 816 can provide structural support for the segments 802 as the flexible member 804 transitions from the deformable state to the shape-set state.

In this way, the rounded corners 816 can provide a smooth transition and prevent slipping between the segments 802. The segments 802 are shown to have the ridges 828 on both the top sides 806 and on bottom sides 902. The ridges 828 include an inner portion 904 which is furthest from the top sides 806 and the bottom sides 902 where the ridges 828 open.

The tapered surfaces 826 of the leading segment 822 and the intermediary segments 824 are depicted extending down from an inner portion 904 of the ridges 828 near the top sides 806 and the bottom sides 902 of the intermediary segments 824 to near conduits 906.

The tapered surfaces 826 in the straight configuration are depicted as planar tapered surfaces extending as a plane from the leading segment 822 and over the two intermediary segments 824 next to the leading segment 822. In other contemplated embodiments, the tapered surfaces 826 can be curved and cover only part of a segment 802.

The conduits 906 can provide a channel for the flexible member 804 to traverse through each of the segments 802. It is contemplated that the conduits 906 can be arranged in two vertically arranged channels. The conduits 906 of each of the segments 802 can be arranged to open near the conduits 906 of each adjacent segment 802 enabling the flexible member 804 to pass through each of the segments 802 and into the adjacent segment 802.

Figure 10:
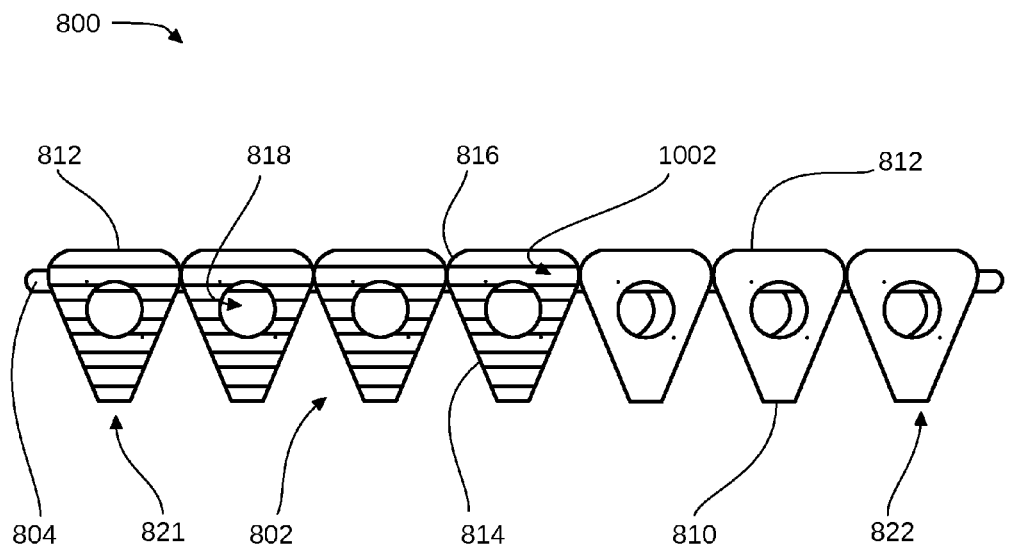
FIG. 10 is a top view of the spinal fusion system of FIG. 9.

Referring now to FIG. 10, therein is shown a top view of the spinal fusion system 800 of FIG. 9. The flexible member 804 is depicted extending through the segments 802 and through the cavities 818 of the segments 802. The flexible member 804 is located near the radially outer sides 812 of the segments 802.

It is contemplated that the location of the flexible member 804 near the radially outer sides 812 can be located along a neutral axis, that is an open end 910 of FIG. 9 and a looped end 912 of FIG. 9 of the flexible member 804 can maintain the same distance from the terminal segment 821 and the leading segment 822 when the flexible member 804 is in the curved shape-set configuration as well as the straight configuration. That is, the neutral axis providing a constant length of the flexible member 804 within the circumferentially closed through holes based on the segments 802 touching continuously in the straight configuration and the curved configuration.

The segments 802 can include walls 1002 that terminate in the radially oriented sides 814, radially inner sides 810, or the radially outer sides 812 and the cavities 818. The flexible member 804 is shown extending partially through the walls 1002 of the segments 802 near the radially outer sides 812.

It is contemplated that the conduits 906 of FIG. 9 extending through the walls 1002 of the segments 802, can provide extra guidance for the transition of the flexible member 804 between the deformable state and the shape-set state.

Figure 11:
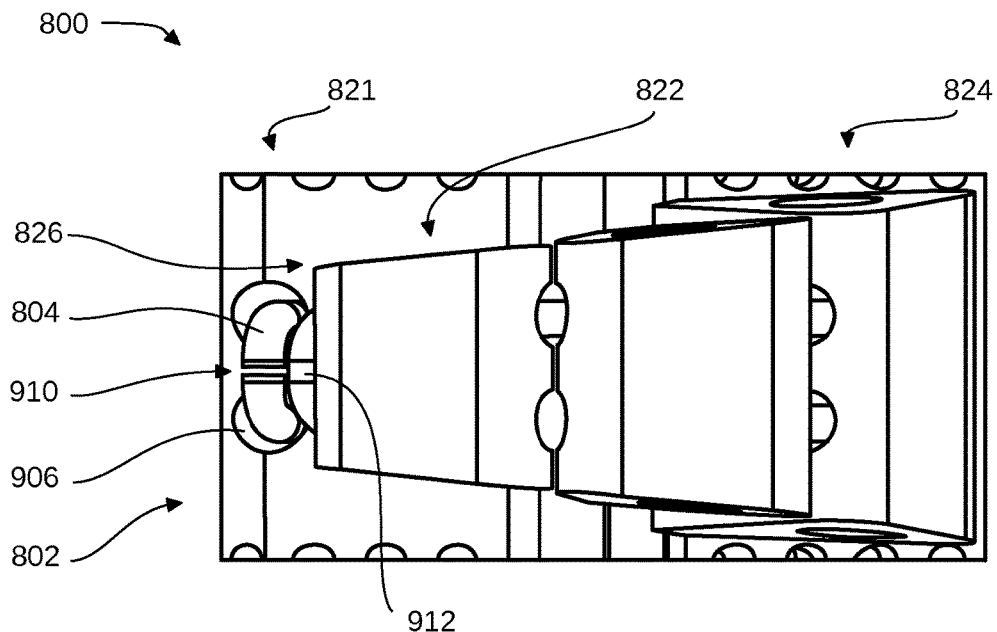
FIG. 11 is a side view of the spinal fusion system of FIG. 8.

Referring now to FIG. 11, therein is shown a side view of the spinal fusion system 800 of FIG. 8. The flexible member 804 is shown extending through the conduits 906 of the segments 802 from the terminal segment 821 to the leading segment 822. The conduits 906 are depicted as circumferentially, closed through holes laterally larger than the flexible member 804.

The flexible member 804 is further shown having a looped end 912 and an open end 910. The open end 910 maintains a space between arms of the flexible member 804 while the looped end 912 loops around the leading segment 822.

It is contemplated that the open end 910 could be connected by welding, or threaded connections. The tapered surfaces 826 are shown in the shape-set configuration as different angled planes for the leading segment 822 and the two next intermediary segments 824 rather than the single angled plane shown in the straight configuration of FIG. 10.

Figure 12:
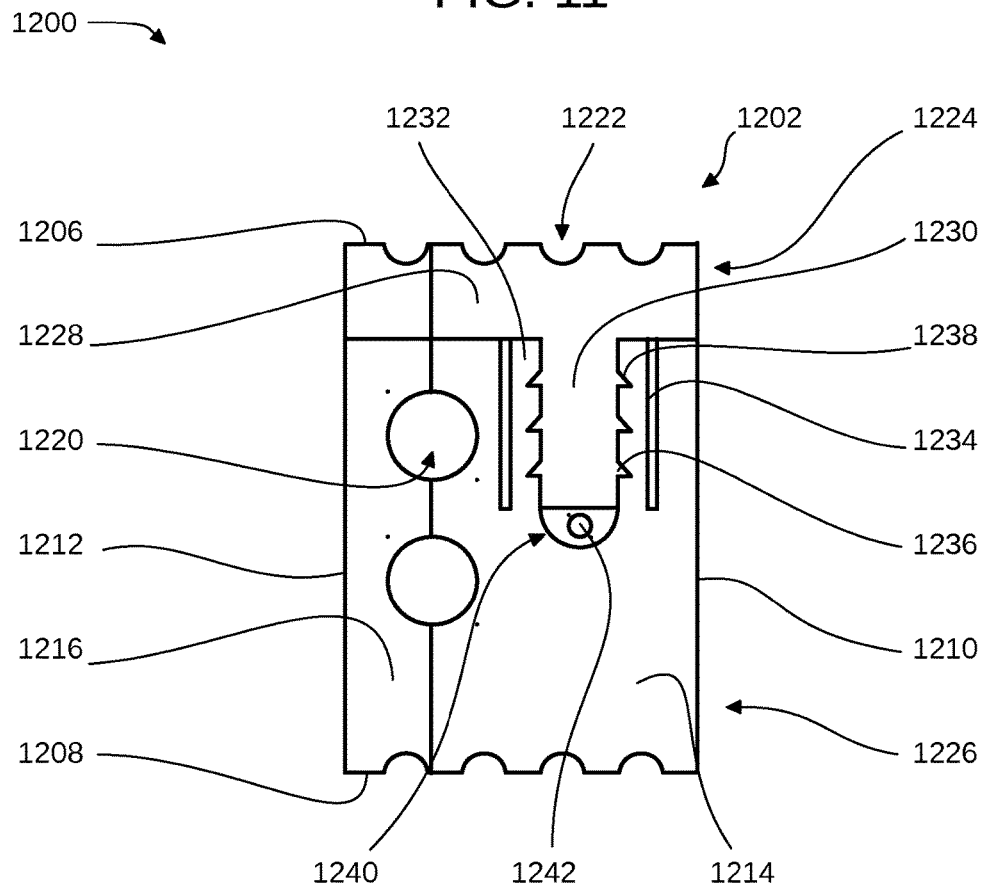
FIG. 12 is a side view of a segment for a spinal fusion system in a fourth embodiment in an un-distracted configuration.

Referring now to FIG. 12, therein is shown a side view of a segment 1202 for a spinal fusion system 1200 in a fourth embodiment in an un-distracted configuration. The segment 1202 is depicted having a top side 1206, a bottom side 1208, a radially inner side 1210, a radially outer side 1212, radially oriented sides 1214, and rounded corners 1216.

The segment 1202 includes conduits 1220 extending through the radially oriented sides 1214 and the rounded corners 1216. The conduits 1220 can allow the flexible member 104 of FIG. 1 to be inserted therethrough and connect the segment 1202 to other segments.

The top side 1206 and the bottom side 1208 of the segment 1202 include ridges 1222 to minimize movement or migration after a spinal fusion procedure. The segment 1202 is shown including a top portion 1224 and a bottom portion 1226.

The top portion 1224 includes a top platform 1228 and a height fixation extension 1230. The top platform 1228 includes the top side 1206 with the ridges 1222 of the segment 1202. The top platform 1228 can sit flush on top of the bottom portion 1226.

The height fixation extension 1230 can extend into a height fixation receptacle 1232 within the bottom portion 1226. The height fixation receptacle 1232 can be positioned apart from the bottom portion 1226 along vertical sides 1234 providing space for the height fixation receptacle 1232 to expand laterally.

The height fixation extension 1230 includes angled protrusions 1236 that can fit into corresponding angled recesses 1238. It is contemplated that as the height fixation extension 1230 moves up within the height fixation receptacle 1232, the angled protrusions 1236 will move out of the angled recesses 1238 and force the height fixation receptacle 1232 laterally outward and allow the angled protrusions 1236 to catch on the next level of the angled recesses 1238.

Once the angled protrusions 1236 reach the next level of the angled recesses 1238, the height fixation receptacle 1232 can collapse back toward the height fixation extension 1230 and lock the height fixation extension 1230 into the height fixation receptacle 1232. When the height fixation extension 1230 is locked in the height fixation receptacle 1232, the height fixation extension 1230 is prevented from moving back down into the height fixation receptacle 1232.

The top portion 1224 and the bottom portion 1226 can be spread apart increasing the total height of the segment 1202 and distracting the vertebra during a spinal fusion procedure. The angled recesses 1238 of the height fixation receptacle 1232 and the angled protrusions 1236 of the height fixation extension 1230 can lock the bottom portion 1226 in a distracted position away from and spaced apart from the top portion 1224.

The height fixation receptacle 1232 can further include a height adjustment hole 1240 extending through the radially oriented side 1214 of the segment 1202. The height adjustment hole 1240 can be formed by the bottom portion of the height fixation receptacle 1232 and the bottom portion of the height fixation extension 1230.

The height adjustment hole 1240 can be rounded in the bottom of the height fixation receptacle 1232 and flat at the bottom of the height fixation extension 1230. Within the height adjustment hole 1240 an expandable member 1242 can be inserted.

The expandable member 1242 can be a balloon or lever to increase the vertical distance between the bottom portion 1226 and the top portion 1224. The expandable member 1242 can expand in the height adjustment hole 1240 forcing the height fixation extension 1230 out of the height fixation receptacle 1232 thereby increasing the height of the segment 1202. The bottom portion 1226 includes the height fixation receptacle 1232.

Figure 13:
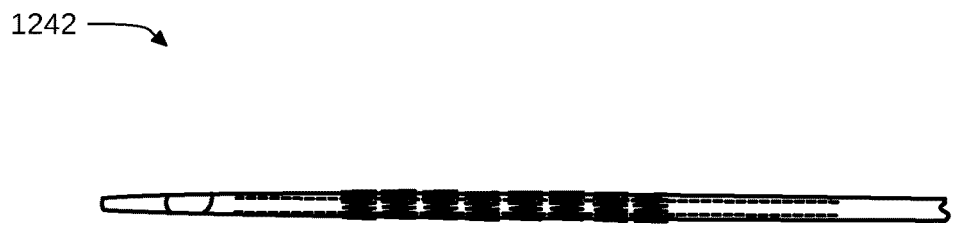
FIG. 13 is a side view of the expandable member of FIG. 12.

Referring now to FIG. 13, therein is shown a side view of the expandable member 1242 of FIG. 12. The expandable member 1242 is shown as an elongated balloon in a collapsed state.

It is contemplated that the expandable member 1242 can be inserted into all of the segments 102 of FIG. 1. It is further contemplated that only a selected individual segment 102 of FIG. 1 could include the height fixation extension 1230 of FIG. 12, and these could be individually extended with the expandable member 1242.

Figure 14:
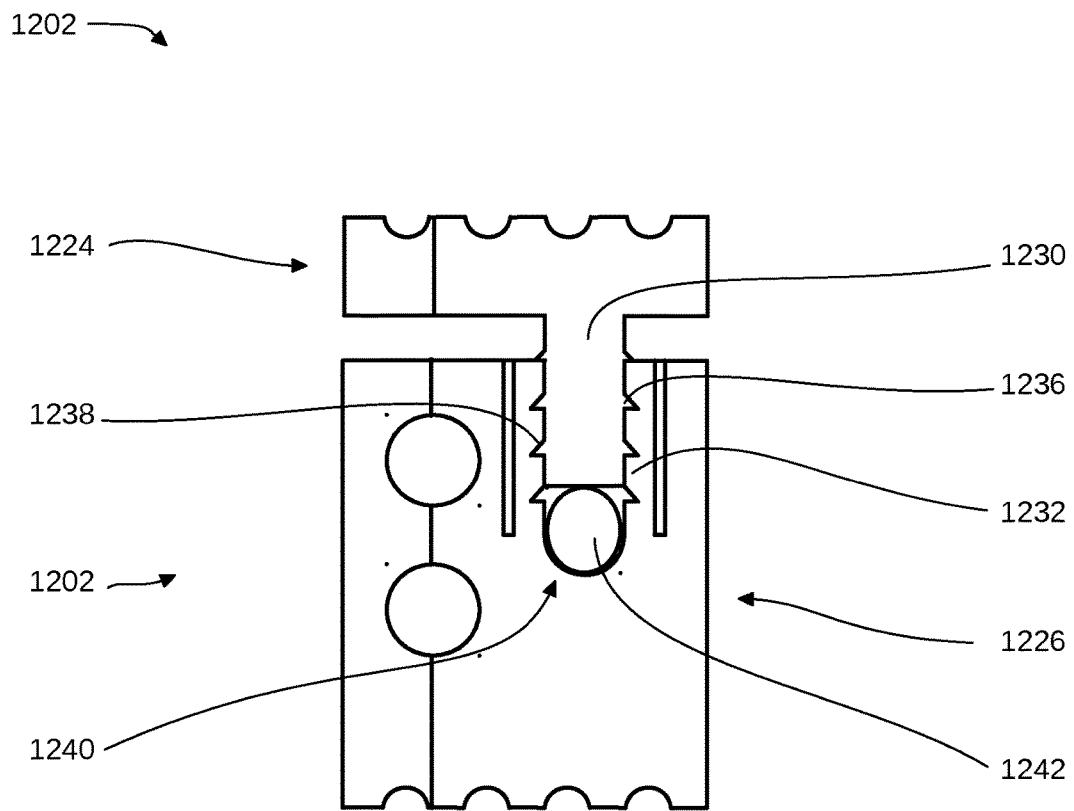
FIG. 14 is a side view of the segment of FIG. 12 in a distracted configuration.

Referring now to FIG. 14, therein is shown a side view of the segment 1202 of FIG. 12 in a distracted configuration. The top portion 1224 and the bottom portion 1226 are shown spaced apart and the height fixation extension 1230 extending out of the height fixation receptacle 1232 and locked into a higher vertical position with the angled protrusions 1236 and the angled recesses 1238.

The expandable member 1242 within the height adjustment hole 1240 is depicted as enlarged in a vertical direction as well as a lateral direction. The expandable member 1242 can force the height fixation extension 1230 up out of the height fixation receptacle 1232 by direct physical contact therebetween.

Figure 15:
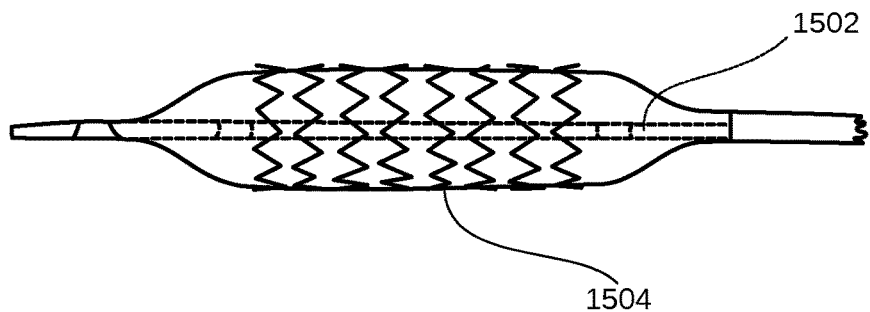
FIG. 15 is a side view of the expandable member of FIG. 14.

Referring now to FIG. 15, therein is shown a side view of the expandable member 1242 of FIG. 14. The expandable member 1242 can include a guide 1502 to direct the expandable member 1242 into the height adjustment hole 1240 of FIG. 14.

The expandable member 1242 is further shown having an expandable support 1504 around the expandable member 1242. It is contemplated that the expandable support 1504 could be left within the height adjustment hole 1240 to provide additional support for the height fixation extension 1230.

In an alternative embodiment, it is contemplated that the expandable member 1242 could expand and force the bottom portion 1226 of FIG. 14 and the top portion 1224 of FIG. 14 apart then be collapsed and removed entirely.

Figure 16:
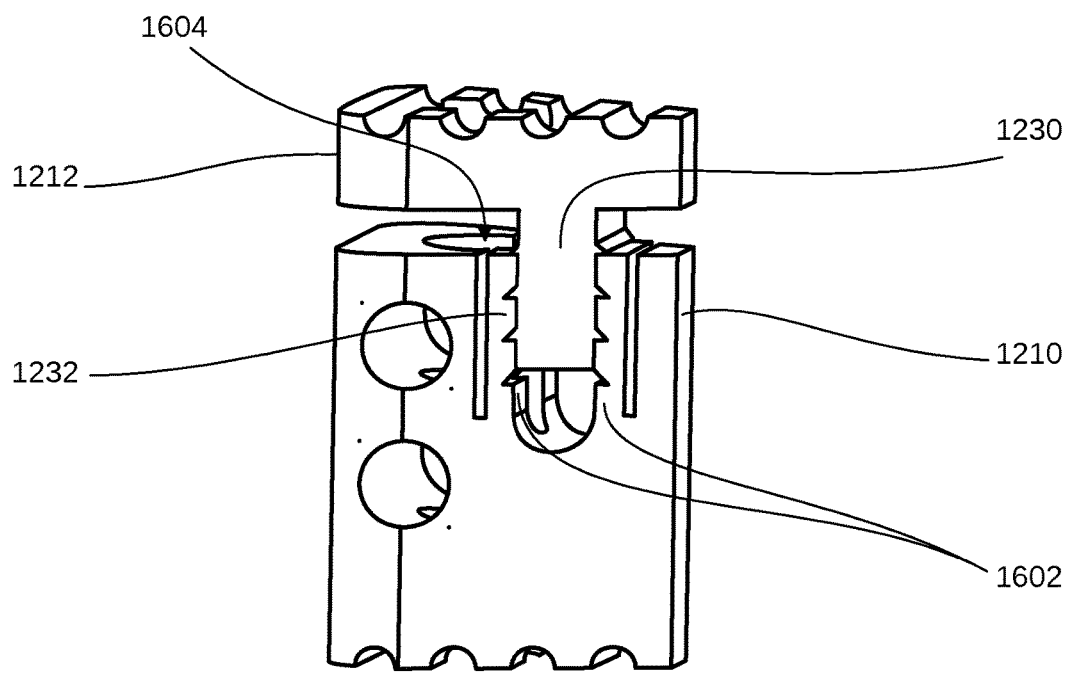
FIG. 16 is an isometric view of the segment of FIG. 14.

Referring now to FIG. 16, therein is shown an isometric view of the segment 1202 of FIG. 14. The segment 1202 is depicted with the height fixation receptacle 1232 having three vertical elements 1602.

The first of the vertical elements 1602 near the radially inner side 1210 can be a single unitary piece in contact with the height fixation extension 1230. The second and third vertical elements 1602 near the radially outer side 1212 can be spaced apart by the cavity 1604.

Referring now to FIG. 17, therein is shown a side view of a segment 1702 in a fifth embodiment. The segment 1702 is depicted having a top side 1704 and a bottom side 1706 angled to compensate for a lordotic angle. The top side 1704 and the bottom side 1706 are angled from a radially outer side 1708 to a shorter radially inner side 1710.

Referring now to FIG. 18, therein is shown a side view of a segment 1804 in a sixth embodiment. The segment 1802 is depicted having a top side 1804 and a bottom side 1806 angled to compensate for a kyphotic angle. The top side 1804 and the bottom side 1806 are angled from a radially outer side 1808 to a shorter radially inner side 1810.

Referring now to FIG. 19, therein is shown a block diagram 1900 for a method of manufacturing a spinal fusion system. The method includes providing segments including a first segment and a second segment in a block 1902; and coupling the first segment to the second segment with a flexible member, the flexible member configured to have a deformable state based upon a temperature of the flexible member being below a transition temperature range or based upon a stress being applied to the flexible member, and the flexible member configured to enter a shape-set state from the deformable state based on the temperature of the flexible member rising above the transition temperature range, or based upon the stress being removed from the flexible member and the temperature of the flexible member being above the transition temperature range in a block 1904.

In some contemplated embodiments the segments can be machined or molded out of a bio-compatible material. It is contemplated that the bio-compatible material should exhibit sufficient mechanical strength to withstand the bio-mechanical loads during spinal fusion procedures.

In some contemplated embodiments, the flexible member can be shape-set by constraining the flexible member on a mandrel that represents the shape-set configuration. The flexible member can then be heated along with the shape-setting mandrel to a temperature between 400-550 degrees Celsius.

When the flexible member has thermally stabilized at the shape-setting temperature, the flexible member can be removed from the heat source and immediately quenched water. The flexible member can then be removed from the shape-setting mandrel. Once the flexible member has been quenched, the segments can be threaded onto the flexible member.

The flexible member can be trimmed and the open end welded together. The segments and the flexible member can then be loaded onto the insertion guide, that is relatively straight and rigid, by deforming the flexible member. The flexible member, the segments, and the insertion guide can then be sterilized prior to use.

Thus, it has been discovered that the spinal fusion system furnishes important and heretofore unknown and unavailable solutions, capabilities, and functional aspects. The resulting configurations are straightforward, cost-effective, uncomplicated, highly versatile, accurate, sensitive, and effective, and can be implemented by adapting known components for ready, efficient, and economical manufacturing, application, and utilization.

While the spinal fusion system has been described in conjunction with a specific best mode, it is to be understood that many alternatives, modifications, and variations will be apparent to those skilled in the art in light of the preceding description. Accordingly, it is intended to embrace all such alternatives, modifications, and variations, which fall within the scope of the included claims. All matters set forth herein or shown in the accompanying drawings are to be interpreted in an illustrative and non-limiting sense.

What is claimed is:

1. A method of manufacturing a spinal fusion system comprising:
   providing segments including a first segment and a second segment, the segments having circumferentially closed through holes and guide holes both extended therethrough, the circumferentially closed through holes including a first conduit vertically offset from a second conduit;
   coupling the first segment to the second segment with a flexible member threaded through the circumferentially closed through holes, the flexible member configured to have a deformable state based upon a temperature of the flexible member being below a transition temperature range or based upon a stress being applied to the flexible member, and the flexible member configured to enter a shape-set state from the deformable state based on the temperature of the flexible member rising above the transition temperature range, or based upon the stress being removed from the flexible member and the temperature of the flexible member being above the transition temperature range; and inserting a mandrel into the guide holes, the mandrel having a rounded tip extended beyond the segments, the rounded tip useful for distracting vertebra during a spinal fusion procedure, the guide holes positioned nearer to radially inner sides of the segments than the flexible member, the radially inner sides being sides of the segments located closer to a center of an arc than radially outer sides of the segments based on the segments being in a curved configuration, and the radially inner sides having a shorter length than the radially outer sides.

2. The method of claim 1 further comprising shape-setting the flexible member to have a curved shape based on the flexible member being in the shape-set state.

3. The method of claim 1 wherein:
providing the segments includes providing at least one of the segments having a cavity; and further comprising:
filling the cavity with an osteogenic material.

4. The method of claim 1 wherein providing the segments includes providing at least one of the segments having a ridge on a top side, a bottom side, or a combination thereof.

5. The method of claim 1 wherein providing the segments includes providing at least one of the segments having a tapered surface on a top side, a bottom side, or a combination thereof and the tapered surface is angled for distracting vertebrae during a spinal fusion procedure.

6. The method of claim 1 wherein providing segments having the first conduit and the second conduit include providing the first conduit and the second conduit laterally larger than the flexible member.

7. A method of manufacturing a spinal fusion system comprising:
providing segments including a first segment and a second segment, the segments having circumferentially closed through holes and guide holes both extended therethrough, the circumferentially closed through holes including a first conduit vertically offset from a second conduit; and coupling the first segment to the second segment with a flexible member threaded through the circumferentially closed through holes, the flexible member having ends extended from the first conduit and the second conduit of the segments, the flexible member configured to have a martensite state based upon a temperature of the flexible member being below a martensite finish temperature or based upon stress being applied to the flexible member, the flexible member configured to enter an austenite state from the martensite state based on the temperature of the flexible member rising above an austenite finish temperature, or based upon the stress being removed from the flexible member and the temperature of the flexible member being above the austenite finish temperature, and the circumferentially closed through holes positioned within the segments at a neutral axis, the neutral axis providing a constant length of the flexible member within the circumferentially closed through holes based on the segments touching continuously in a straight configuration and a curved configuration; and inserting a mandrel into the guide holes, the mandrel having a rounded tip extended beyond the segments, the rounded tip useful for distracting vertebra during a spinal fusion procedure, the guide holes positioned nearer to radially inner sides of the segments than the flexible member, the radially inner sides being sides of the segments located closer to a center of an arc than radially outer sides of the segments based on the segments being in the curved configuration, and the radially inner sides having a shorter length than the radially outer sides.

8. The method of claim 7 wherein coupling the first segment to the second segment includes coupling the first segment to the second segment with the flexible member configured to have the austenite finish temperature below thirty-seven degrees Celsius.

9. The method of claim 7 further comprising coupling the first segment and the second segment to the mandrel configured to maintain the flexible member in the martensite state by keeping the flexible member under stress based on the first segment and the second segment being in a straight configuration.

10. The method of claim 7 wherein providing the segments includes providing at least one of the segments having an angled surface to compensate for a lordotic angle or kyphotic angle.

11. The method of claim 7 wherein providing the segments includes providing at least one of the segments with a top portion having a height fixation extension and with a bottom portion having a height fixation receptacle, the height fixation extension mated to the height fixation receptacle and configured to lock the top portion and the bottom portion in a distracted state.

12. A spinal fusion system comprising:
segments including a first segment and a second segment, the segments having circumferentially closed through holes and guide holes both extended therethrough, the circumferentially closed through holes including a first conduit vertically offset from a second conduit; and a flexible member threaded through the circumferentially closed through holes, the first segment coupled to the second segment with the flexible member, the flexible member configured to have a deformable state based upon a temperature of the flexible member being below a transition temperature range or based upon a stress being applied to the flexible member, and the flexible member configured to enter a shape-set state from the deformable state based on the temperature of the flexible member rising above the transition temperature range, or based upon the stress being removed from the flexible member and the temperature of the flexible member being above the transition temperature range; and a mandrel inserted into the guide holes, the mandrel having a rounded tip extended beyond the segments, the rounded tip useful for distracting vertebra during a spinal fusion procedure, the guide holes positioned nearer to radially inner sides of the segments than the flexible member, the radially inner sides being sides of the segments located closer to a center of an arc than radially outer sides of the segments based on the segments being in a curved configuration, and the radially inner sides having a shorter length than the radially outer sides.

13. The system of claim 12 wherein the flexible member is shape-set to have a curved shape based on the flexible member being in the shape-set state.

14. The system of claim 12 wherein at least one of the segments have a cavity filled with an osteogenic material.

15. The system of claim 12 wherein at least one of the segments have a ridge on a top side, a bottom side, or a combination thereof.

16. The system of claim 12 wherein at least one of the segments have a tapered surface on a top side, a bottom side, or a combination thereof and the tapered surface is angled for distracting vertebrae during a spinal fusion procedure.

17. The system of claim 12 wherein at least one of the segments have an angled surface to compensate for a lordotic angle or kyphotic angle.

18. The system of claim 12 wherein at least one of the segments include a top portion having a height fixation extension and include a bottom portion having a height fixation receptacle, the height fixation extension mated to the height fixation receptacle and configured to lock the top portion and the bottom portion in a distracted state.

19. The system of claim 12 wherein the flexible member having ends extended from the first conduit and the second conduit of the segments, the flexible member configured to have a martensite state based upon the temperature of the flexible member being below a martensite finish temperature or based upon stress being applied to the flexible member, and the flexible member configured to enter an austenite state from the martensite state based on the temperature of the flexible member rising above an austenite finish temperature, or based upon the stress being removed from the flexible member and the temperature of the flexible member being above the austenite finish temperature, and the circumferentially closed through holes positioned within the segments at a neutral axis, the neutral axis providing a constant length of the flexible member within the circumferentially closed through holes based on the segments touching continuously in a straight configuration and the curved configuration.

20. The system of claim 19 wherein the austenite finish temperature is below thirty-seven degrees Celsius.

21. The system of claim 19 further comprising the mandrel coupled to the first segment and the second segment, and the mandrel configured to maintain the flexible member in the martensite state by keeping the flexible member under stress based on the first segment and the second segment being in a straight configuration.

22. The system of claim 12 wherein the first conduit and the second conduit are laterally larger than the flexible member.

* * * * *